United States Patent
Yoshikawa et al.

(10) Patent No.: US 11,685,704 B2
(45) Date of Patent: Jun. 27, 2023

(54) TRIHYDROXYBENZENE PRODUCTION METHOD

(71) Applicant: MITSUI CHEMICALS, INC., Tokyo (JP)

(72) Inventors: Osamu Yoshikawa, Tokyo (JP); Masaki Yabe, Tokyo (JP); Mitsufumi Wada, Chiba (JP); Yusuke Ito, Niigata (JP); Hideki Ouchi, Niigata (JP)

(73) Assignee: MITSUI CHEMICALS, INC., Tokyo (JP)

( * ) Notice: Subject to any disclaimer, the term of this patent is extended or adjusted under 35 U.S.C. 154(b) by 5 days.

(21) Appl. No.: 17/286,867

(22) PCT Filed: Oct. 24, 2019

(86) PCT No.: PCT/JP2019/041723
§ 371 (c)(1),
(2) Date: Apr. 20, 2021

(87) PCT Pub. No.: WO2020/085435
PCT Pub. Date: Apr. 30, 2020

(65) Prior Publication Data
US 2021/0331993 A1 Oct. 28, 2021

(30) Foreign Application Priority Data

Oct. 25, 2018 (JP) ................................. 2018-201017

(51) Int. Cl.
| | | |
|---|---|---|
| C07C 37/07 | (2006.01) | |
| C07C 37/72 | (2006.01) | |
| C12P 7/26 | (2006.01) | |
| C12P 7/22 | (2006.01) | |
| C12R 1/19 | (2006.01) | |

(52) U.S. Cl.
CPC .............. *C07C 37/07* (2013.01); *C07C 37/72* (2013.01); *C12P 7/22* (2013.01); *C12P 7/26* (2013.01); *C12Y 402/03124* (2015.07); *C12R 2001/19* (2021.05)

(58) Field of Classification Search
CPC ..... C07C 37/07; C07C 37/72; C12R 2001/19; C12P 7/22; C12P 7/26; C12N 9/88; C12Y 402/03124
See application file for complete search history.

(56) References Cited

U.S. PATENT DOCUMENTS

| | | |
|---|---|---|
| 2010/0015672 A1 | 1/2010 | Takagi et al. |
| 2011/0207187 A1 | 8/2011 | Tokuda et al. |
| 2012/0046498 A1 | 2/2012 | Kitagawa et al. |
| 2014/0256960 A1 | 9/2014 | Takagi et al. |

FOREIGN PATENT DOCUMENTS

| | | |
|---|---|---|
| EP | 1 865 056 A1 | 12/2007 |
| EP | 2 426 098 A1 | 3/2012 |
| JP | 5373066 B2 | 12/2013 |
| WO | 2006109479 A1 | 10/2006 |
| WO | 2006112000 A1 | 10/2006 |
| WO | 2010053052 A1 | 5/2010 |
| WO | 2015005451 A1 | 1/2015 |

OTHER PUBLICATIONS

"Extraction in Theory and Practice (Part 1)", https://www.chem.ucla.edu/~bacher/Specialtopics/extraction.html, Dec. 2013, 6 pages. (Year: 2013).*
Chad A. Hansen, et al., "Deoxygenation of Polyhydroxybenzenes: An Alternative Strategy for the Benzene-Free Synthesis of Aromatic Chemicals", Journal of the American Chemical Society, American Chemical Society, May 2, 2002, vol. 124, No. 21, pp. 5926-5927. (2 pages).
Seibutsu-Kogaku, "Deoxy-scyllo-inosose(DOI)", 2015 (month unknown), vol. 93, pp. 533-535, with a partial English translation. (5 pages).
Katsumi Kakinuma, et al., "An expeditious chemo-enzymatic route from glucose to catechol by the use of 2-deoxy-scyllo-inosose synthase", Tetrahedron Letters, Elsevier Science Ltd., 2000 (month unknown), vol. 41, No. 12, pp. 1935-1938. (4 pages).
The Extended European Search Report dated Oct. 6, 2022, by the European Patent Office in corresponding European Patent Application No. 19875909.4. (5 pages).
Cohen, Saul G., "The Acetolysis of Esters," Journal of the American Chemical Society, Aug. 1, 1944, vol. 66, No. 8, pp. 1395-1397.

\* cited by examiner

*Primary Examiner* — Rosalynd A Keys
(74) *Attorney, Agent, or Firm* — Buchanan, Ingersoll & Rooney PC

(57) ABSTRACT

A method of producing THB with improved efficiency is provided. Provided is a method of producing trihydroxybenzene (THB), the method comprising a step of heating a bacterial culture liquid comprising deoxy-scyllo-inosose (DOI) at a high temperature of no lower than 80° C. to obtain a product solution comprising trihydroxybenzene (THB).

6 Claims, 4 Drawing Sheets

TRIHYDROXYBENZENE PRODUCTION METHOD

TECHNICAL FIELD

The present disclosure relates to a method of producing trihydroxybenzene (THB).

BACKGROUND

Deoxy-scyllo-inosose (2-deoxy-scyllo-inosose; abbreviated as DOI) is a compound which can be derivatized to a variety of useful chemicals. In general, industrially useful chemicals, especially six-membered carbon ring compounds, are in many cases manufactured chemically from the raw materials of the fossil resources, especially petroleum. However, DOI is known to be synthesizable from sugars through a bioprocess using bacteria expressing a specific enzyme (WO 2006/109479 (Patent Document 1), WO 2010/053052 (Patent Document 2), WO 2015/005451 (Patent Document 3)), and therefore DOI represents a particularly attractive chemical in the interest of breaking away from the fossil resource dependency and protecting the global environment.

Thus, the cellulosic plant materials such as woodchips can be broken down to monosaccharides such as glucose by using known technologies, and the monosaccharides can then be converted to DOI by the above-mentioned bioprocess, to realize the chemical product manufacturing characterized by the effective utilization of the non-fossil resources.

Among the further intermediate compounds that can be derivatized from DOI, one of the most typical is trihydroxybenzene (THB). THB is a compound produced by a dehydration reaction from DOI (a total of two molecules of water are removed from one molecule of DOI). THB can be further derivatized to useful compounds such as quercitol, carbaglucose, catechol, adipic acid derivatives, hydroquinone, trimethoxybenzene, trimethoxybenzoic acid phenyl ester, and sesamol. These THB-derived useful compounds can be used in various applications such as diabetes-treating drugs, nylons, photo chemicals, polymerization inhibitors, Li secondary battery additives, cellulose film additives, and antidepressant drugs (Seibutsu-Kogaku, vol. 93, 533-535, 2015 (Non-Patent Document 1)).

CITATION LIST

Patent Documents

Patent Document 1: WO 2006/109479
Patent Document 2: WO 2010/053052
Patent Document 3: WO 2015/005451

Non-Patent Documents

Non-Patent Document 1: Seibutsu-Kogaku, vol. 93, 533-535, 2015

SUMMARY OF INVENTION

Technical Problem

In order to obtain THB from the DOI synthesized by the bacteria-mediated bioprocess, the following process is conventionally carried out: Purified DOI in a powder form is obtained by following many steps including acidification of the culture medium, centrifugation, filtration, cation exchange, anion exchange, drying, concentration, methanol co-boiling, drying, crystallization, and filter drying; the purified powder DOI is then dissolved in water; and it is heated e.g. at 170° C. for 2 hours to finally obtain the product THB. However, the many steps like these are labor-intensive and time-consuming, significantly increasing the production costs. Improvement of the efficiency of the THB production by simplification of the manufacturing steps and/or by increase of the production yields is desired.

The present disclosure provides a method of producing THB with improved efficiency.

Solution to Problem

The present inventors have discovered that THB can be produced at high yields by directly heating the culture liquid of the bacteria which have synthesized DOI. The present disclosure is based on this discovery.

The present disclosure includes at least the following embodiments.

[1] A method of producing trihydroxybenzene (THB), the method comprising a step of heating a bacterial culture liquid comprising deoxy-scyllo-inosose (DOI) at a high temperature of no lower than 80° C. to obtain a product solution comprising trihydroxybenzene (THB).

[2] The method according to [1], wherein the bacterial culture liquid comprises at least 1 g/L DOI accumulated from culturing DOI-synthesizing bacteria.

[3] The method according to [2], further comprising, before the heating, a step of culturing the DOI-synthesizing bacteria in a liquid culture medium under a DOI-synthesizing condition, wherein the liquid culture medium after the culturing provides the bacterial culture liquid.

[4] The method according to [3], further comprising, before the heating, a step of removing the bacteria from the bacterial culture liquid.

[5] The method according to any of [1] to [4], wherein the high temperature is from 90 to 300° C.

[6] The method according to any of [1] to [5], wherein the heating at the high temperature is carried out for at least 30 seconds.

[7] The method according to any of [1] to [6], further comprising a step of separating the trihydroxybenzene (THB) from the product solution.

[8] The method according to [7], wherein the step of separating comprises solvent extraction.

[9] The method according to [8], wherein the solvent in the solvent extraction is ethyl acetate.

According to the embodiments of the present disclosure, the efficiency of producing THB can be significantly improved. That is, the number of steps included in the process from bacterial DOI synthesis to THB production can be reduced to achieve significant simplification, and part or all of the process can be carried out in a continuous manner.

DESCRIPTION OF EMBODIMENTS

Figure 1:
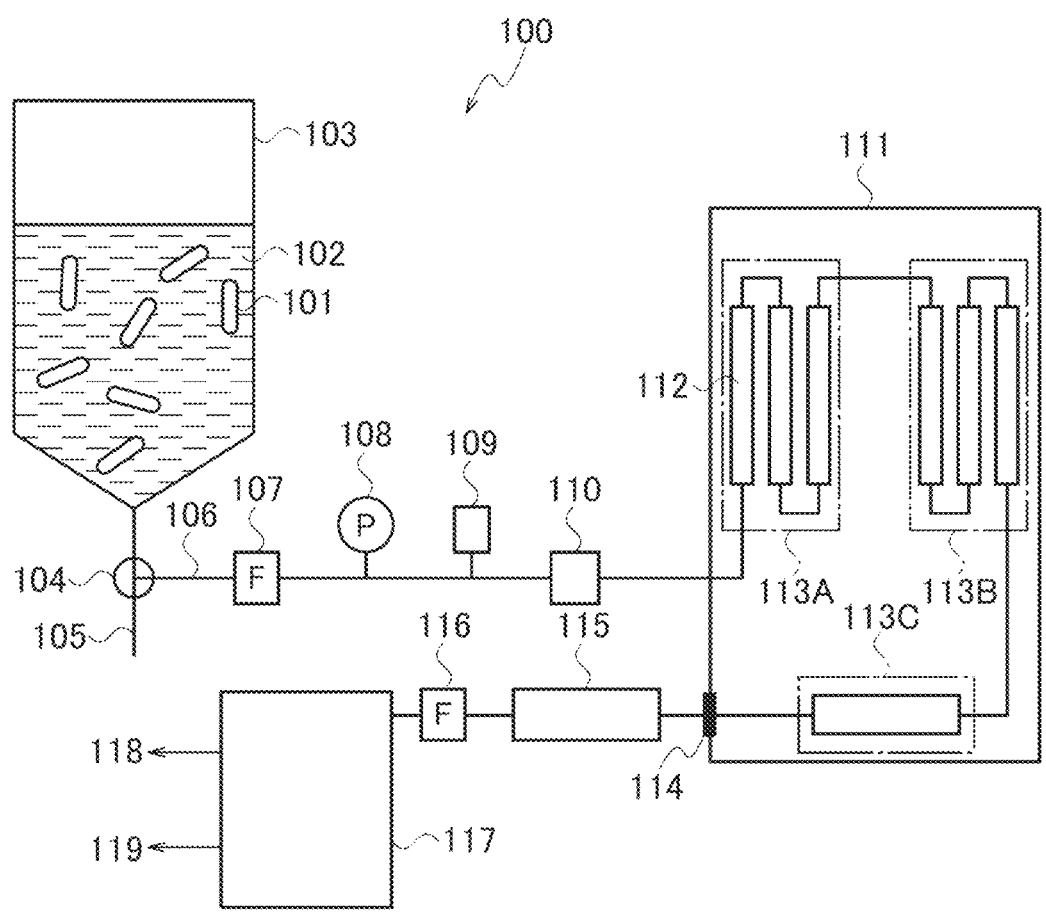
FIG. 1 shows a schematic of a THB production system according to one embodiment.

In one aspect, the present disclosure provides a method of producing trihydroxybenzene (THB), the method comprising a step of heating a bacterial culture liquid comprising deoxy-scyllo-inosose (DOI) at a high temperature of no lower than 80° C. to obtain a product solution comprising trihydroxybenzene (THB).

The structure of deoxy-scyllo-inosose (DOI) is shown below.

[Chemical Formula 1]

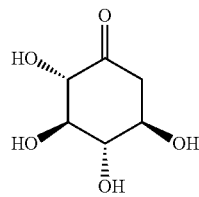

The structure of trihydroxybenzene (THB) is shown below.

[Chemical Formula 2]

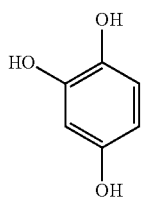

The structure shown above corresponds to 1,2,4-trihydroxybenzene, but the THB produced in the present embodiment may comprise 1,2,3-trihydroxybenzene (pyrogallol) in addition to 1,2,4-trihydroxybenzene. Further, the product solution may also comprise catechol.

The concentration of DOI in the bacterial culture liquid to be heated, i.e. the concentration of DOI in the bacterial culture liquid at the stage prior to the heating, is preferably 1 g/L or higher, more preferably 10 g/L or higher, and still more preferably 50 g/L or higher. There is no particular upper limit to the DOI concentration, but the concentration is typically no higher than 100 g/L, for example no higher than 90 g/L or no higher than 80 g/L.

The bacterial culture liquid is a conditioned liquid culture medium comprising DOI, which is obtained after culturing the DOI-synthesizing bacteria in a liquid culture medium under the DOI-synthesizing condition. The liquid culture media suitable for culturing the DOI-synthesizing bacteria are known to a person skilled in the art, or can be prepared by a person skilled in the art based on ordinary knowledge, and typically the liquid culture media are capable of supporting the culture at a cell density of $10^7$ cells/mL or higher, preferably $10^8$ cells/mL or higher, during a stationary phase. As known to a person skilled in the art, the liquid culture media for culturing bacteria typically comprise carbon source (especially sugars), nitrogen source (such as amino acids), vitamins, inorganic salts, etc. In the present embodiment, it has been confirmed that the similar results can be obtained even if specific ingredients for the media vary, as long as the liquid culture media can support the culture at a relatively high cell density and the DOI synthesis as described above. The sugars other than glucose can be metabolized into glucose, but the liquid culture media may preferably comprise glucose itself because it means the substrate for the DOI synthesis is directly provided, thereby improving the efficiency.

An example of typical liquid culture media that can be used to obtain the bacterial culture liquid of the present embodiment is the YE medium, which may comprise: 50 to 200 g of BD Bacto Tryptone (pancreatic digest of casein) (104 g in 2X YE medium); 60 to 260 g of BD Bacto Yeast Extract (water-soluble extract of the yeast) (130 g in 2X YE medium); 15 to 60 g of NaCl (32.5 g in 2X YE medium); 200 to 800 g of glucose (377 to 390 g in 2X YE medium); 150 to 650 g of mannitol (335 g in 2X YE medium); and optionally antibiotics such as ampicillin, phytic acid, and/or small amounts of additives such as anti-foaming agent (e.g. no more than 5 g in total), per 6.5 L of water. Phytic acid is an additional component that can improve the DOI production of the bacteria, and for example 1 to 20 g of a 50% (w/w) phytic acid aqueous solution can be added to the above-mentioned amount of YE medium.

Another specific example of the liquid culture medium (CSL medium) comprises: 150 to 700 g of CSL (corn steep liquor) (325 g in a standard medium); 1000 to 5000 g of glucose (2010 g in a standard medium); 1000 to 5000 g of fructose (2010 g in a standard medium); 100 to 500 g xylose (200 g in a standard medium); 50 to 500 g of ammonium sulfide (170 g in a standard medium); 20 to 200 g of ammonium chloride (78.2 g in a standard medium); 20 to 200 g of magnesium sulfate heptahydrate (78.2 g in a standard medium); 40 to 200 g of dipotassium hydrogenphosphate (91 g in a standard medium); 40 to 200 g of potassium dihydrogenphosphate (91 g in a standard medium); and 2 to 10 g of iron(II) sulfate heptahydrate (4.55 g in a standard medium) per 52.6 kg of water. The CSL medium may further comprise 40 to 200 g of 50% (w/w) phytic acid (91 g in a standard medium) per 52.6 kg of water. The CSL medium may comprise an anti-foaming agent (e.g. 5 to 30 g of Adeka nol anti-foaming agent per above-mentioned amount of the CSL medium).

During the culturing, part or all of the culture medium ingredients may be replenished at any time. For example, a sugar component may be preferably replenished in the course of the culturing.

The bacterial culture liquid to be heated may or may not contain the bacterial cells. Thus, in one embodiment, the bacterial culture liquid to be heated is the liquid culture medium after culturing the bacteria therein, in which the bacteria are still present or from which the bacteria have been removed. In the present specification, the term "solution" (including "aqueous solution") means a liquid in which at least one substance different from the solvent is dissolved or suspended. A solution may comprise an insoluble substance or a solid substance suspended therein. The insoluble substance and the solid substance in this context may include biological cells.

Thus, the bacterial culture liquid to be heated, i.e. the bacterial culture liquid at the stage prior to the heating, may contain the bacterial cells which synthesized the DOI. For example, the method of the present embodiment may be carried out by culturing the bacteria in a liquid culture medium to synthesize DOI from the sugars, and then directly heating the liquid culture medium containing the bacteria and the DOI (i.e. the bacterial culture liquid) at the high temperature, without inserting the steps of removing the bacteria and purifying the DOI. In such an embodiment, the production of THB and inactivation/sterilization of the used bacteria can be performed concurrently. Thus, the overall procedure is substantially simplified, and furthermore, it is advantageous from a biosafety, as well as sanitation, standpoint.

In one embodiment, the method further comprises a step of culturing the DOI-synthesizing bacteria in a liquid culture medium under a DOI-synthesizing condition, before the step of heating the bacterial culture liquid. The liquid culture medium after the culturing provides the bacterial culture liquid to be heated.

The bacterial culture liquid to be heated may have gone through culturing preferably for 12 hours or longer, more preferably 16 hours or longer, for example 24 hours or longer, or 32 hours or longer. In the culturing, a cell density of preferably $10^7$ cells/mL or higher, more preferably $10^8$ cells/mL or higher may be achieved within 24 hours starting from a cell density of $10^4$ cells/mL or lower. Through the culturing of the DOI-synthesizing bacteria, preferably 1 g/L or more, more preferably 10 g/L or more, still more preferably 50 g/L or more of DOI may accumulate in the bacterial culture liquid. The culturing temperature is typically 25 to 38° C., and 30 to 37° C. may be preferable. The culturing condition for allowing the bacteria to synthesize DOI may be adjusted by a person skilled in the art based on ordinary knowledge.

DOI-synthesizing bacteria are known to a person skilled in the art, or identifiable or obtainable by a person skilled in the art based on publicly available information. Specific examples of species of such bacteria include, but are not limited to, *Escherichia coli*, *Bacillus circulans*, *Bacillus amyloliquefaciens*, *Bacillus subtilis*, *Corynebacterium glutamicum*, and *Geobacillus stearothermophilus*. *Escherichia coli* is especially preferable. The bacteria preferably express a 2-deoxy-scyllo-inosose-synthesizing enzyme. Most preferably, the DOI-synthesizing bacterium is *Escherichia coli* expressing a 2-deoxy-scyllo-inosose-synthesizing enzyme. Preferable examples of the 2-deoxy-scyllo-inosose-synthesizing enzymes include the product of the btrC gene from *Bacillus circulans* (Patent Document 1), but a person skilled in the art will understand that the products of the homologous genes from other bacteria or the enzymes having alterations relative to the naturally occurring sequences may be alternatively used as long as they retain the DOI-synthesizing activity. Such genes are preferably introduced exogenously by a genetic engineering technique, although they may also be endogenous. The means for increasing and/or optimizing the gene expression, such as the choice of the plasmid vector, the choice of the promoter, codon optimization and so on, are known to a person skilled in the art. For example, the promoter may be a constitutive promoter or an inducible promoter.

The host bacteria in which the 2-deoxy-scyllo-inosose-synthesizing enzyme is introduced may have alteration, addition, or deletion of other gene(s). For example, the DOI yield may be increased by using a host *Escherichia coli* in which one or more, or all, of pgi, zwf, and pgm (which are the genes that can metabolize glucose-6-phosphate, the substrate for DOI-synthesis, into other compounds) and/or rmf (which is the gene involved in the repression of the protein synthesis during the stationary growth phase) has been destroyed (Patent Document 1). In such cases, it may become preferable to add a non-glucose carbon source, such as mannitol, to the culture medium. However, by adding the sucrose hydrolase gene (cscA) to *E. coli* for example, inexpensive sucrose can be used as nutrition source while allowing efficient DOI synthesis from glucose (Patent Document 2). It has been shown that at least several tens of grams of DOI per liter of the culture medium can be accumulated by these systems (Patent Documents 1 to 3).

The liquid culture medium after the DOI synthesis by the bacteria (i.e. the bacterial culture liquid) can comprise, in addition to the 2-deoxy-scyllo-inosose (DOI), small amounts (e.g. in total no more than 20%, no more than 15%, no more than 10%, or no more than 5% of the weight of the 2-deoxy-scyllo-inosose (DOI)) of one or more related compounds selected from the following group: 1-epi-DOI, $\alpha,\beta$-unsaturated keton, (+)-vibo-quercitol, and scyllo-quercitol.

The bacterial culture liquid may be heated while still containing the bacteria, or alternatively, a step of removing the bacteria cells from the bacterial culture liquid may be added prior to the heating. This step can help avoid the possibility that the purity of the product solution is reduced, or the reaction is inhibited, by the large amount of insoluble matter that would be released from the heated cells. The techniques used in the step of removing the bacteria cells from the bacterial culture liquid can be selected by a person skilled in the art from any known techniques as appropriate, including for example filtration and centrifugation. Filtration is preferable because it can be carried out by relatively simple machinery.

In order to remove the cells, a filter having a cutoff of 1 μm or smaller, for example a filter with 0.2 μm pore size, may be used. Multiple filters having different pore sizes may be combined. By selecting the pore size of the filter, other substances besides the cells may also be removed from the bacterial culture liquid before the heating. For example, by appropriate filtering to remove any ingredients unnecessary for the THB synthesis from the bacterial culture liquid, the purity of the THB in the product solution after the heating may be improved. Any ingredients unnecessary for the THB synthesis may also be removed by salting out.

The temperature of the "high temperature" for heating the bacterial culture liquid is no lower than 80° C. At a temperature lower than 80° C., the DOI conversion reaction per se may occur, but it is believed that the conversion efficiency would not be sufficiently high. The temperature of the high temperature is preferably no lower than 90° C., more preferably no lower than 100° C., more preferably no lower than 130° C., still more preferably no lower than 140° C., especially preferably no lower than 160° C., and most preferably no lower than 170° C.

There is no particular upper limit for the high temperature, but it is usually no higher than 300° C., or no higher than 200° C. The high temperature is typically 130 to 180° C. The high temperature can be combined with a high pressure above the atmospheric pressure. Such a high pressure can be for example no higher than 1 MPa, no higher than 0.8 MPa, no higher than 0.5 MPa, or no higher than 0.2 MPa.

The duration of the heating of the bacterial culture liquid at the high temperature may vary depending on the temperature used and the THB yields desired, but it is usually at least 30 seconds, preferably at least 1 minute, more preferably at least 2 minutes, more preferably at least 5 minutes, more preferably at least 10 minutes, and still more preferably at least 30 minutes. The heating may be carried out for 1 hour or longer, 2 hours or longer, or 4 hours or longer. The heating may be continuous over the above duration, or, the heating may be intermittent such that the cumulative time in which the temperature reaches the high temperature amounts to the above duration. There is no particular upper limit to the heating duration, and the duration may be for example no longer than 24 hours, no longer than 4 hours, no longer than 2 hours, no longer than 1 hour, no longer than 30 minutes, or no longer than 10 minutes.

The heating of the bacterial culture liquid at a high temperature can be achieved by using any methods known to a person skilled in the art, for example injecting hot gas (steam) or hot liquid into the bacterial culture liquid, contacting the bacterial culture liquid with a solid heat source, heating the inner wall of the vessel or tube containing the bacterial culture liquid, applying an electrical current to the bacterial culture liquid, and/or applying a microwave to the bacterial culture liquid.

The atmosphere around the bacterial culture liquid when it is heated may preferably be air, an inert gas such as nitrogen and argon, or a mixture thereof. The atmosphere around the bacterial culture liquid when it is heated is preferably a substantially hydrogen ($H_2$) free atmosphere. A substantially hydrogen free atmosphere may for example have a hydrogen volume concentration of less than 1 ppm. Also, preferably, the heating of the bacterial culture liquid is carried out substantially in the absence of a metal catalyst, or a reduction catalyst, such as palladium, rhodium, ruthenium, platinum, iridium, nickel, cobalt, and copper.

A "product solution" means a solution which is obtained after the heating of the bacterial culture liquid and in which THB is dissolved or suspended.

A filtering or centrifugation treatment may be carried out to remove any impurities from the product solution. These treatments can be especially meaningful following the heating of the bacterial culture liquid containing the bacterial cells, because in that case the product solution may comprise a large amount of insoluble matter originating from the denatured cells.

The method of the present embodiment may further comprise a step of separating THB from the product solution. For the separation of THB, any known methods can be utilized as appropriate. Preferably, THB is extracted from the product solution by solvent extraction. The solvent extraction may be repeated for one or more times. The extraction solvent is preferably ethyl acetate or methyl acetate, and especially preferably ethyl acetate, but not necessarily limited to these. The volume of the extraction solvent used in the extraction is preferably equal to or larger than the volume of the product solution. As understood by a person skilled in the art, solvent extraction may be carried out by mixing the product solution with an organic solvent and then separating an organic layer and an aqueous layer, and then collecting the organic layer comprising THB. A water-soluble salt may be added to the product solution to perform the solvent extraction. For example, the yields may be improved if the solvent extraction is performed after adding the sub-saturation concentration sodium chloride to the product solution. The yields may also be improved if the solvent extraction is performed after lowering the pH of the product solution by adding an acid, for example hydrochloric acid, to the product solution. The pH is preferably brought down to lower than 2, more preferably to lower than 1.5, and still more preferably to lower than 1. If the THB sample after the separation contains insoluble matter, it can be removed by filtration, for example.

The THB sample after the separation preferably has a THB content of no lower than 50%, more preferably no lower than 60%, more preferably no lower than 70%, still more preferably no lower than 80%, and especially preferably no lower than 90%, by the dry weight after removal of any insoluble matter and the solvent. The THB sample after the separation preferably has a catechol content of no higher than 5%, more preferably no higher than 3%, more preferably no higher than 2%, and especially preferably no higher than 1.5%, by the dry weight after removal of any insoluble matter and the solvent.

(a) From the stage of DOI synthesis by the culturing of the bacteria to the stage of THB production by the heating at the high temperature, and/or (b) from the stage of THB production to the stage of THB separation, may be carried out in a continuous manner. These stages may also be carried out in batches.

In another aspect, the present disclosure provides a system for producing trihydroxybenzene (THB), the system comprising: a culture vessel which holds a liquid culture medium comprising DOI-synthesizing bacteria to culture the bacteria and produce a bacterial culture liquid; and a heating apparatus which is connected to the culture vessel and heats the bacterial culture liquid at a high temperature of no lower than 80° C. to produce a product solution comprising trihydroxybenzene (THB).

This system is suited for carrying out the method according to the above-described aspect of the present disclosure. Thus, in the present specification, the descriptions provided for the method embodiments can be applied to the system embodiments, and vice versa. For example, the liquid culture medium is typically capable of supporting the culture at a cell density of $10^7$ cells/mL or higher, preferably $10^8$ cells/mL or higher, during a stationary phase, as described above. The bacteria are also as described above.

The culture vessel may be equipped with accessory installation(s) for providing a condition suitable for culturing the bacteria. For example, the culture vessel may have one or more of: a stirring apparatus for stirring the culture medium; a shaking apparatus for shaking the culture medium; an aeration apparatus for aerating the culture medium; or a thermal apparatus for warming the culture medium. The culture vessel may be connected to a liquid culture medium supply line which supplies part or all of the fresh liquid culture medium components into the culture vessel. In one embodiment, this liquid culture medium supply line has a switch valve, thereby the culture vessel can switch between connecting to the liquid culture medium supply line and connecting to the liquid conveyance tube described below.

The culture vessel may be connected to the heating apparatus via a liquid conveyance tube. The heating apparatus in this case heats the liquid inside the heating apparatus as the liquid is conveyed from the culture vessel. For example, the heating apparatus may have a structure which comprises continuous heating passages in the inside, such that the bacterial culture liquid passing through the heating passages gets heated. The heating passages may heat the liquid culture medium by, for example, injecting hot gas or hot liquid into the bacterial culture liquid passing, or by heating the inner wall of the passage or a solid heat source placed within the passage, but possible heating methods are not limited to these. The hot gas may be for example heated air, steam, or nitrogen. The hot liquid may be for example heated water or fresh liquid culture medium. The heating temperature, retention time, and flow speed within the heating passages may be adjusted at will. The heating passages may have a plurality of heating zones which may be set at different temperatures. The heating apparatus may comprise an outlet for collecting the product solution comprising THB produced by the heating.

The culture vessel may be connected to the heating apparatus via a cell removal apparatus which removes the bacterial cells from the bacterial culture liquid. The cell removal apparatus may comprise a filter, or a centrifuge. A cell removal apparatus comprising a filter for removing the cells is preferable. A plurality of filters having different pore sizes may be provided in the cell removal apparatus, and any unnecessary components besides the cells may also be removed at this stage. The cell removal apparatus may be provided in the middle of the liquid conveyance tube.

The liquid conveyance tube may have one or more of: a cell removal apparatus; a pump for conveying the liquid; a safety valve for preventing excessive internal pressure (e.g. 10 bar or higher); or a flow rate control apparatus for controlling the flow rate. The types and number of these accessory installations, as well as the order of their placement along the direction of the liquid flow, can be determined by a person skilled in the art as appropriate.

Alternatively, the heating apparatus may be an integrated heating apparatus which heats the bacterial culture liquid inside the culture vessel itself. The heating in this case may be achieved for example by injecting hot gas or hot liquid into the culture vessel, or by heating the inner wall of the culture vessel or a solid heat source placed within the culture vessel, but possible heating methods are not limited to these. The hot gas may be for example heated air, steam, or nitrogen. The hot liquid may be for example heated water or fresh liquid culture medium.

The heating temperature and the heating time provided by the heating apparatus are as described above for the embodiments of the methods of producing THB.

The heating apparatus (including the culture vessel it is integrated with, in the case of the integrated heating apparatus) may be connected to a purification apparatus which removes any solid matter and insoluble matter from the product solution. The purification apparatus may comprise a filter or a centrifuge, for example. When the bacterial culture liquid heated had contained the bacterial cells, a large amount of insoluble matter originating from the denatured cells may be present in the product solution, and this purification apparatus can remove the insoluble matter. The purification apparatus may comprise a plurality of filters having different pore sizes. Likewise, the heating apparatus may be connected to a cooling apparatus for reducing the temperature of the liquid. The liquid after the heating at the high temperature may be cooled to a room temperature, for example, and this cooling apparatus can facilitate the cooling.

Further, the heating apparatus (including the culture vessel it is integrated with, in the case of the integrated heating apparatus) may be connected to a separation apparatus which separates the THB product from the product solution. The separation apparatus is preferably connected downstream of the above-described purification apparatus. The separation apparatus may for example comprise a known solvent extraction apparatus such as centrifugal extractor, mixer-settler, micro reactor, flow reactor, and pulsed column. The solvent extraction apparatus may comprise an organic layer outlet for discharging the organic layer comprising THB. The solvent extraction apparatus may further comprise an aqueous layer outlet for discharging the aqueous layer.

The heating apparatus may be connected to the separation apparatus via a liquid conveyance tube. This liquid conveyance tube may also comprise accessory installation(s) as described above, such as a pump, a safety valve, a cooling apparatus, a purification apparatus, and a flow rate control apparatus, in any number and order of placement.

The system of the present embodiment as a whole may be integrated into a single apparatus.

In a further aspect, the present disclosure provides a method of producing THB using the THB production system of the present embodiment.

An example of the system according to the present embodiment is shown in FIG. 1. In the system 100 of this example, the DOI-synthesizing bacteria 101 and the liquid culture medium 102 are held in the culture vessel 103, and the culturing is carried out inside the culture vessel 103. That is, the liquid culture medium 102 becomes the bacterial culture liquid 102'. The culture vessel 103 can, by means of the switch valve 104, be connected to either of the liquid culture medium supply line 105 or the liquid conveyance tube 106. The liquid conveyance tube 106 is equipped with the cell removal apparatus 107 having a filter, the pump 108 for conveying the liquid (i.e. the bacterial culture liquid 102' after the filtration), the safety valve 109 for preventing excessive internal pressure (e.g. 10 bar or higher), and the flow rate control apparatus 110 for controlling the flow rate, and connected to the heating apparatus 111. Inside the heating apparatus 111, the bacterial culture liquid is heated as it passes through the heating passage 112. In this example, three heating zones 113A, B and C are provided inside the heating apparatus 111, each having one or more heating passages and capable of heating the liquid culture medium at temperatures different from each other. The bacterial culture liquid having undergone the heating at the high temperature becomes a product solution comprising THB, and exits the heating apparatus 111 from the outlet 114. The outlet 114 is connected to the separation apparatus 117 comprising a centrifugal extractor, via a cooling apparatus 115 that cools the product solution and a purification apparatus 116 that comprises a filter and removes solid matter and insoluble matter from the product solution. The separation apparatus 117 adds an organic solvent (e.g. ethyl acetate) to the product solution to perform extraction, and discharges the organic layer 118 and the aqueous layer 119. THB is separated in the organic layer 118.

Figure 2:
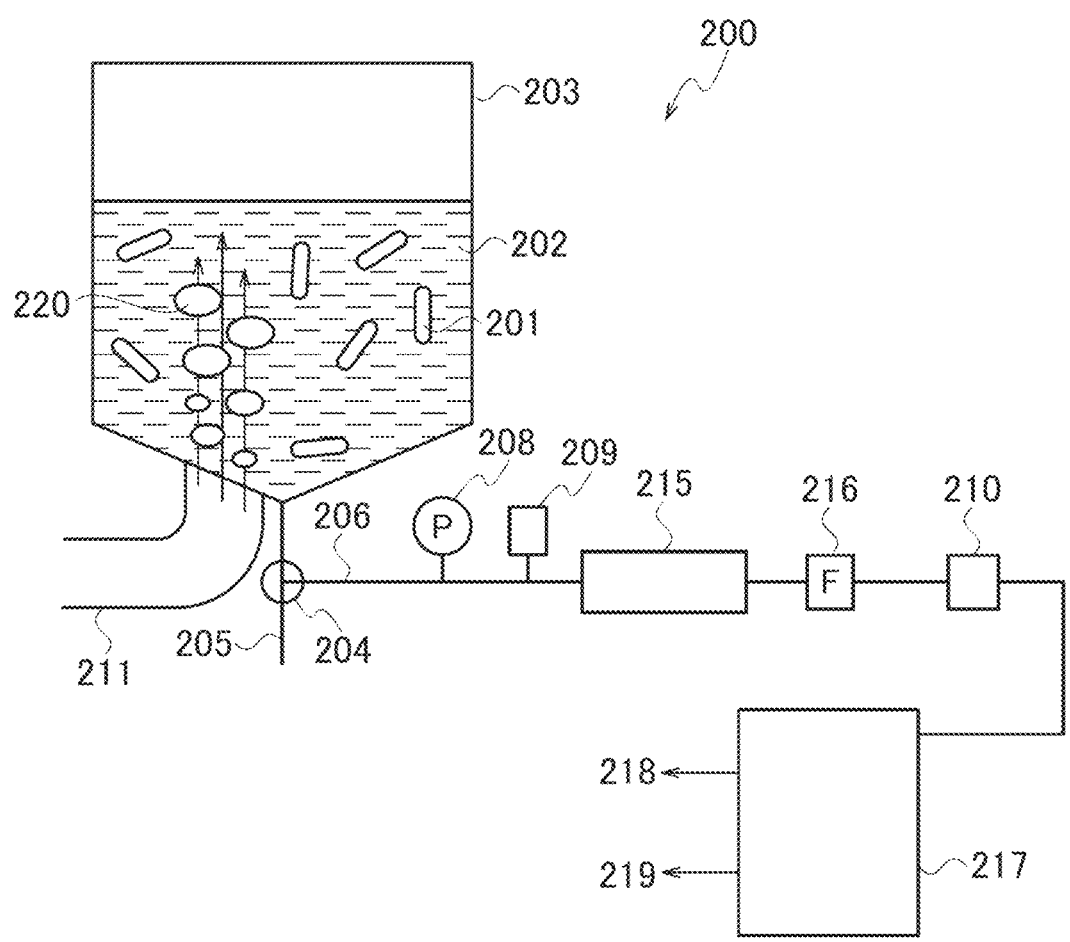
FIG. 2 shows a schematic of a THB production system according to another embodiment.

Another example of the system according to the present embodiments is shown in FIG. 2. In the system 200 of this example, again, the DOI-synthesizing bacteria 201 and the liquid culture medium 202 are held in the culture vessel 203, and the culturing is carried out inside the culture vessel 203. That is, the liquid culture medium 202 becomes the bacterial culture liquid 202'. The culture vessel 203 is equipped with the integrated heating apparatus 211. The integrated heating apparatus 211 heats the cultured liquid culture medium 202, i.e. the bacterial culture liquid 202', to a high temperature by injecting the hot gas 220 into the culture vessel 203. Thus, the bacterial culture liquid 202' is converted to a product solution comprising THB inside the culture vessel 203. The culture vessel 203 can, by means of the switch valve 204, be connected to either of the liquid culture medium supply line 205 or the liquid conveyance tube 206. The liquid conveyance tube 206 is equipped with a pump 208 for conveying the product solution, a safety valve 209 for preventing excessive internal pressure, a cooling apparatus 215 for cooling the product solution, a purification apparatus 216 that comprises a filter and removes solid matter and insoluble matter from the product solution, and a flow rate control apparatus 210 for controlling the flow rate, and connected to the separation apparatus 217 comprising a centrifugal extractor. The separation apparatus 217 adds an organic solvent (e.g. ethyl acetate) to the product solution to perform extraction, and discharges the organic layer 218 and the aqueous layer 219. THB is separated in the organic layer 218.

EXAMPLES

Figure 3A:
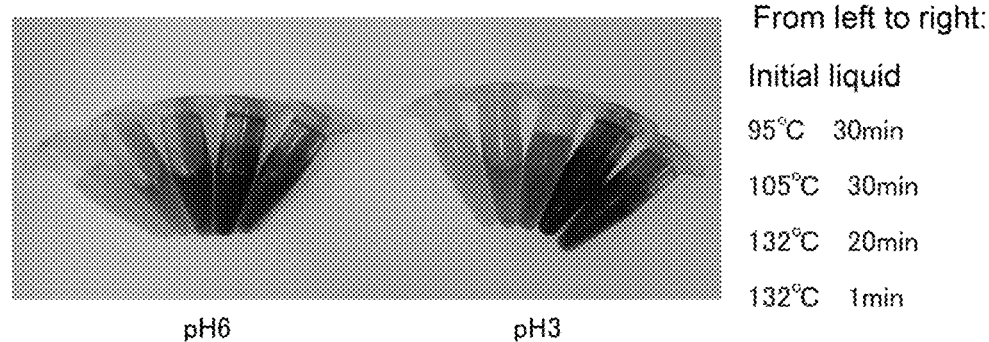
FIG. 3(a) shows the appearances and FIG. 3(b) shows the DOI contents of the DOI fermentation liquids (initial liquids) and the liquids obtained by heating them.
Figure 3B:
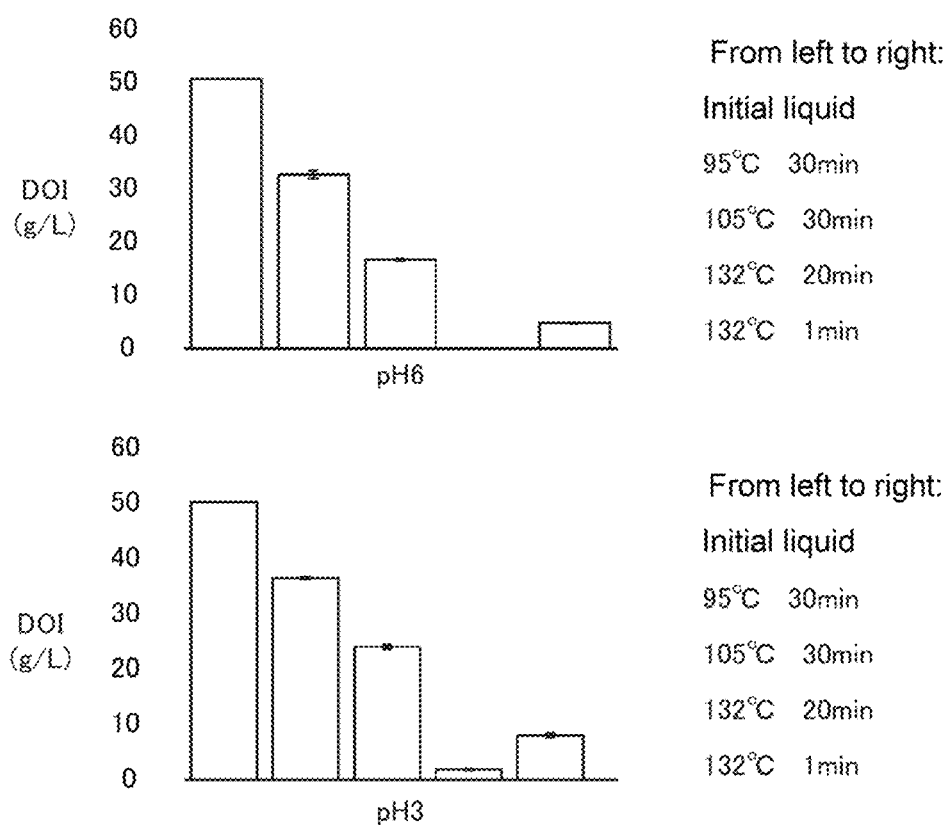

E. coli expressing a 2-deoxy-scyllo-inosose synthesizing enzyme (btrC gene product) under a DOI-synthesizing condition was cultured in the 2X YE culture medium, and when the bacterial culture liquid after the culturing (hereafter referred to as a DOI fermentation liquid) was subsequently subjected to a deactivation process at about 80° C., a color change in the DOI fermentation liquid was noticed. This led the inventors to speculate the possibility that a conversion reaction from DOI to THB might have occurred in the DOI fermentation liquid. FIG. 3(a) shows the appearances of the DOI fermentation liquids (initial liquids) at pH 6 or pH 3, and the same liquids heated at 95° C. for 30 minutes, heated at 105° C. for 30 minutes, heated at 132° C. for 20 minutes, and heated at 132° C. for 10 minutes; and FIG. 3(b) shows their DOI contents. The reductions in the DOI contents concomitant with the color changes of the DOI fermentation liquids were apparent, suggesting the production of THB. The samples after the heating were analyzed by the liquid chromatography (column: YMC-Pac ODS-AQ; elution: 10 mM acetic acid aqueous solution/acetonitrile=3/97; detector: evaporative light scattering detector) and mass spectrometry, which confirmed the production of THB. For example, in the DOI fermentation liquid sample which had been heated at 132° C. for 20 minutes, it was revealed that about 30% of the DOI had been converted to THB, and about 50% had been converted to other dehydration products.

Next, using a vessel and a heating apparatus essentially as shown in FIG. 1, a purified-DOI aqueous solution (DOI concentration 70 g/L) and a DOI fermentation liquid (filtered with a 0.2 μm MF membrane; DOI concentration 59.1 g/L) were heated under different test conditions, and the compounds comprised in the liquids after the heating were analyzed, and the results were compared. This DOI fermentation liquid had been obtained by culturing the E. coli expressing the btrC gene, as described above, in the CSL culture medium for 32 to 40 hours. The results of the analyses are shown in Table 1 below.

In Table 1, the purified-DOI aqueous solution samples and the DOI fermentation liquid samples having the same test conditions are shown in the same lines. The DOI retention rate refers to the percentage of the DOI remaining after the heating, out of the DOI that was comprised in the sample before the heating. The 1,2,4-THB conversion rate refers to the percentage of the DOI converted to 1,2,4-THB, out of the DOI that was comprised in the sample before the heating (the mono-dehydration product conversion rate is defined in a similar manner). As a side note, the production of 1,2,3-THB was also confirmed in the similar experiment (data not shown). The notation "160° C. for 30 seconds, 5 repeats", for example, means a heating at 160° C. for 30 seconds was repeated for the total of 5 times, i.e. the sample was heated at 160° C. for the accumulative time of 2.5 minutes.

It can be seen from the results of Table 1 that the amount of conversion is increased as the accumulative time of the heating becomes longer (e.g. compare samples 2 to 4 of the purified-DOI aqueous solutions), and the conversion efficiency is improved when the heating temperature is higher (e.g. compare samples 2 and 5, samples 3 and 6, or samples 4 and 7 of the DOI fermentation liquids).

Importantly, under the same heating conditions, the conversion from DOI to THB was achieved at significantly higher efficiency in the DOI fermentation liquids compared to the purified-DOI aqueous solutions. That is, while the THB conversion rate in the purified-DOI aqueous solution sample 2 was 2.33%, the THB conversion rate in the DOI fermentation liquid sample 5 under the same heating condition was 27.19%. Likewise, the THB conversion rate in the purified-DOI aqueous solution sample 3 was 5.23%, but in contrast, the THB conversion rate in the DOI fermentation liquid sample 6 was 43.40%. The THB conversion rate in the purified-DOI aqueous solution sample 4 was 9.55%, but in contrast, the THB conversion rate in the DOI fermentation liquid sample 7 was 54.66%. In the DOI fermentation liquid sample 7, a THB conversion rate exceeding 50% was achieved by the heating at the high temperature of 160° C. for the relatively short accumulative time of 5 minutes. Since similar results were obtained even when the liquid culture media having different ingredients were used, it can be presumed that the liquid environment supporting the bacteria growth itself provides some kind of catalytic effect on the THB conversion reaction.

The THB yields were improved when a DOI fermentation liquid from which the bacteria had been removed by filtration was heated, compared to when a DOI fermentation liquid that had not been filtered was heated, and the THB yields were further improved when the salting out process was combined with the filtration (data not shown).

In another experiment, solvent extraction of THB was tested by using ethyl acetate as an extraction solvent against: a THB aqueous solution; a solution obtained by heating a DOI aqueous solution and containing the THB product; or a

TABLE 1

| Purified-DOI aqueous solution, 70 g/L | | | | | MF (0.2 μm)-filtered DOI fermentation liquid, 59.1 g/L | | | | |
| --- | --- | --- | --- | --- | --- | --- | --- | --- | --- |
| Sample number | Test condition | DOI retention rate | 1,2,4-THB conversion rate | Mono-dehydration product conversion rate | Sample number | Test condition | DOI retention rate | 1,2,4-THB conversion rate | Mono-dehydration product conversion rate |
| Sample 1 | Before heating | 100.0% | | | Sample 1 | Before heating | 100.0% | | |
| | | | | | Sample 2 | 140° C. for 30 sec | 61.1% | 9.06% | 8.95% |
| | | | | | Sample 3 | 140° C. for 30 sec 5 repeats | 58.7% | 19.75% | 17.17% |
| | | | | | Sample 4 | 140° C. for 30 sec 10 repeats | 40.9% | 32.54% | 24.02% |
| Sample 2 | 160° C. for 30 sec | 77.2% | 2.33% | 5.05% | Sample 5 | 160° C. for 30 sec | 45.7% | 27.19% | 21.38% |
| Sample 3 | 160° C. for 30 sec 5 repeats | 70.9% | 5.23% | 12.45% | Sample 6 | 160° C. for 30 sec 5 repeats | 25.9% | 43.40% | 30.21% |
| Sample 4 | 160° C. for 30 sec 10 repeats | 58.3% | 9.55% | 21.37% | Sample 7 | 160° C. for 30 sec 10 repeats | 10.8% | 54.66% | 32.49% | product solution obtained by heating a DOI fermentation liquid. It was confirmed that a single solvent extraction could recover most of the THB. Improvements in the THB recovery rates were observed when the pH of the THB product solution had been reduced to lower than 2 by adding hydrochloric acid before the solvent extraction, or when a sub-saturation concentration of sodium chloride had been added to the THB product solution. The final yields of the extracted THB may vary depending on the conditions and the extent of the THB-producing reaction taking place before the extraction. In an example where the THB product-containing solution used had been obtained by advancing the reaction by heating a DOI aqueous solution at a high temperature of 175° C. for at least 3 hours, it was confirmed that the majority (70% by weight or more, or 90% by weight or more in some cases) of the organic compound solutes dissolved in the organic solvent layer after the extraction was THB, whereas the majority of the impurities remained in the aqueous layer. This result demonstrated that the solvent extraction had a THB-purifying effect. The extraction using a microreactor also recovered THB at high yields, providing the proof-of-principle that from the heating of the bacterial culture liquid to the separation of THB, or from the DOI synthesis by culturing the DOI-synthesizing bacteria followed by the heating of the bacterial culture liquid to the separation of THB, may be carried out in a continuous manner.

Figure 4:
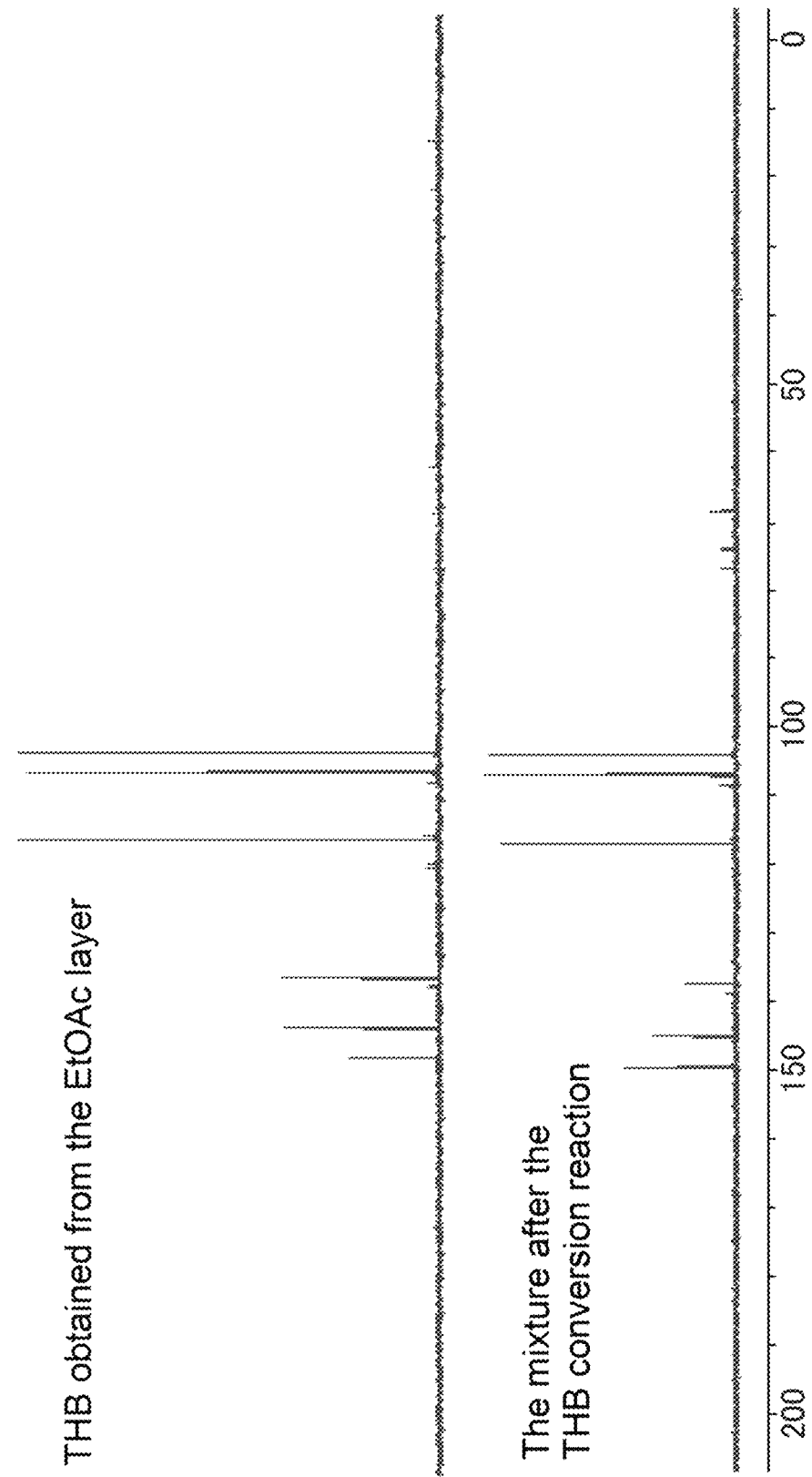
FIG. 4 shows the $^{13}$C-NMR spectra of: the THB product solution obtain from the DOI fermentation liquid (bottom); and the THB sample after the solvent extraction (top).

An example is described below, in which from the DOI synthesis by culturing the DOI-synthesizing bacteria, followed by heating of the bacterial culture liquid (DOI fermentation liquid), to the separation of THB by solvent extraction, was carried out in a continuous manner 150 mL of the DOI fermentation liquid obtained by culturing the DOI-synthesizing bacteria (DOI concentration 60 g/L) was reacted under the condition of 170° C. for 2 hours to convert the DOI to THB. The obtained THB-containing reaction liquid was then filtrated with a membrane filter (0.45 μm) to prepare a THB product solution (the $^{13}$C-NMR spectrum is shown at the bottom of FIG. 4). Then, by using the mixer manufactured by YMC co., ltd., (Deneb Helix type), the THB product solution (1 mL/min) and ethyl acetate (any of the following four conditions: 1 mL/min, 1.5 mL/min, 2 mL/min, and 3 mL/min) were transmitted, and the respective eluates were collected (elution time 1 minute). The ethyl acetate layers were separated from the obtained eluates, then vacuum concentrated, and the THB yields were quantified (all experiments were performed in triplicate). The results are summarized in Table 2 below. When the THB product solution to ethyl acetate ratio was 1:1, the THB yields were on average 74.7%. The yields tended to improve as the proportion of the ethyl acetate became higher, and the average was 86.9% when the THB product solution to ethyl acetate ratio was 1:3. The $^{13}$C-NMR spectrum of the extracted THB sample obtained is shown at the top of FIG. 4.

TABLE 2

Investigation of conditions for extracting THB from DOI fermentation liquids with ethyl acetate by using a microreactor

| THB conc. (mol/L) | THB sol. flow rate (mL/min) | EtOAc flow rate (mL/min) | Extraction time (min) | Total solution volume (mL) | | THB recovered (mg) | THB yield *2 (%) | | Solutes recovered (mg) | Total solute mass (mg) |
|---|---|---|---|---|---|---|---|---|---|---|
| 0.37*1 | 1 | 1 | 1 | 2 | ① | 34.2 | 70.9 | ① | 29.6 | 63.8 |
| | | | | | ② | 38.1 | 79.0 | ② | 25.0 | 63.1 |
| | | | | | ③ | 35.8 | 74.2 | ③ | 29.9 | 65.7 |
| | | | | | Ave. | 36.0 | 74.7 | Ave. | 28.2 | 64.2 |
| | | 1.5 | | 2.5 | ① | 37.1 | 76.9 | ① | 33.3 | 70.4 |
| | | | | | ② | 36.0 | 74.6 | ② | 30.5 | 66.5 |
| | | | | | ③ | 35.6 | 73.8 | ③ | 25.5 | 61.1 |
| | | | | | Ave. | 36.2 | 75.1 | Ave. | 29.8 | 66.0 |
| | | 2 | | 3 | ① | 39.0 | 80.9 | ① | 28.0 | 67.0 |
| | | | | | ② | 41.2 | 85.4 | ② | 25.0 | 66.2 |
| | | | | | ③ | 38.7 | 80.3 | ③ | 28.2 | 66.9 |
| | | | | | Ave. | 39.6 | 82.2 | Ave. | 27.1 | 66.7 |
| | | 3 | | 4 | ① | 39.3 | 81.5 | ① | 25.6 | 64.9 |
| | | | | | ② | 39.9 | 82.7 | ② | 22.7 | 62.6 |
| | | | | | ③ | 46.6 | 96.6 | ③ | 29.8 | 76.4 |
| | | | | | Ave. | 41.9 | 86.9 | Ave. | 26.0 | 68.0 |

*1 The DOI content of the DOI fermentation liquid: 60.2 g/L = 0.37 mol/L (quantified by HPLC)
*2 Calculated by assuming a theoretical THB recovery of 48.2 mg.

The invention claimed is:

1. A method of producing trihydroxybenzene (THB), the method comprising a step of heating a bacterial culture liquid comprising deoxy-scyllo-inosose (DOI) at a high temperature of 130 to 180° C. to obtain a product solution comprising trihydroxybenzene (THB),
   wherein the method further comprises, before the heating, a step of culturing a DOI-synthesizing bacteria in a liquid culture medium under a DOI-synthesizing condition,
   wherein the liquid culture medium after the culturing, without purifying the DOI or only with removal of the bacteria, provides the bacterial culture liquid to be heated.

2. The method according to claim 1, wherein the bacterial culture liquid comprises at least 1 g/L DOI accumulated from culturing DOI-synthesizing bacteria.

3. The method according to claim 1, wherein the heating at the high temperature is carried out for at least 30 seconds.

4. The method according to claim 1, further comprising a step of separating the trihydroxybenzene (THB) from the product solution.

5. The method according to claim 4, wherein the step of separating comprises solvent extraction.

6. The method according to claim 5, wherein the solvent in the solvent extraction is ethyl acetate.

\* \* \* \* \*